(12) United States Patent
Rademacher et al.

(10) Patent No.: US 7,686,975 B2
(45) Date of Patent: Mar. 30, 2010

(54) USE OF ACYLCYCLOHEXANEDIONE DERIVATIVES FOR IMPROVING THE TOLERANCE OF PLANTS TO COLD AND/OR FROST

(75) Inventors: Wilhelm Rademacher, Limburgerhof (DE); Reiner Kober, Fußgönheim (DE); Michaela Schmitz-Eiberger, Bornheim (DE); Georg Noga, Rheinbach (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 368 days.

(21) Appl. No.: 10/549,171

(22) PCT Filed: Mar. 16, 2004

(86) PCT No.: PCT/EP2004/002713

§ 371 (c)(1),
(2), (4) Date: Sep. 16, 2005

(87) PCT Pub. No.: WO2004/082379

PCT Pub. Date: Sep. 30, 2004

(65) Prior Publication Data

US 2007/0066485 A1 Mar. 22, 2007

(30) Foreign Application Priority Data

Mar. 17, 2003 (DE) ................. 103 11 689

(51) Int. Cl.
- C09K 3/18 (2006.01)
- A01G 13/00 (2006.01)
- C08K 5/07 (2006.01)
- A01N 63/00 (2006.01)
- A01N 55/02 (2006.01)
- A01N 37/00 (2006.01)

(52) U.S. Cl. ............... 252/70; 47/2; 106/13; 524/360; 504/118; 504/126; 504/142

(58) Field of Classification Search ......... 504/189, 504/362, 118, 126, 142; 524/360; 106/13; 47/2; 252/70

See application file for complete search history.

(56) References Cited

U.S. PATENT DOCUMENTS

| | | | | | |
|---|---|---|---|---|---|
| 2,961,798 | A | * | 11/1960 | Wells | 47/2 |
| 4,272,276 | A | * | 6/1981 | Szejtli et al. | 504/292 |
| 4,383,845 | A | * | 5/1983 | Rutherford | 71/16 |
| 4,560,403 | A | * | 12/1985 | Motojima et al. | 504/313 |
| 5,510,321 | A | * | 4/1996 | Hirabayashi et al. | 504/289 |
| 6,022,831 | A | | 2/2000 | Evans | |

FOREIGN PATENT DOCUMENTS

| | | | |
|---|---|---|---|
| DE | 44 37 945 A | | 4/1995 |
| DE | 19904703 A1 | * | 8/2000 |
| EP | 0 123 001 A | | 10/1984 |
| EP | 0 348 767 A | | 1/1990 |

OTHER PUBLICATIONS

McArtney, S., Evaluation of Frost Protection Sprays, 2003, URL<http:www.bdmax.co.nz/report.htm>.*
Glacier Frost Protectant, MSDS, Jan. 1, 1999, p. 1-3.*
EnviroShield Products Co., AntiStress Plant Protection Membranes, Jun. 8, 2000, p. 1 and 2.*
Fagerness et al., "Temperature and Trinexapac-ethyl effects on bermudagrass growth, dormancy, and freezing tolerance", Crop Science, vol. 42, No. 3, May 2002, pp. 853-858.
Kurtz et al., "Specific crop management helps rape better during the winter", Pflanzenarzt (53, No. 8, 7-9 2000), vol. 53, No. 8, 2000, p. 9. (with translation).
Robertson et al., "The role of plant growth regulators on the freezing tolerance of winter annual cereals and cell suspension cultures", Advances in Plant Cold Hardiness, 1993, pp. 253-271.
Lalk et al., "Hardening, absscisic acid, proline and freezing resistance in two winter wheat varieties", Physiol. Plant. 63, 287-292, Copenhagen, 1985.
Anonymous: "Max Temperature °C Apr. 2, 1998-Apr. 30, 1998," weatheronline.co.uk, 1998.
Costa et al.: "Prohexadione-Ca (Apogee®): Growth Regulation and Reduced Fire Blight Incidence in Pear," Hort. Science, 36(5): 931-933, 2001.

* cited by examiner

*Primary Examiner*—Johann R Richter
*Assistant Examiner*—Danielle Sullivan
(74) *Attorney, Agent, or Firm*—Rothwell, Figg, Ernst & Manbeck, P.C.

(57) ABSTRACT

The invention relates to the use of acylcyclohexanedione derivatives for improving the tolerance of plants to cold and/or frost.

14 Claims, No Drawings

USE OF ACYLCYCLOHEXANEDIONE DERIVATIVES FOR IMPROVING THE TOLERANCE OF PLANTS TO COLD AND/OR FROST

CROSS REFERENCE TO RELATED APPLICATION

This application is a 35 USC § 371 National Phase Entry Application from PCT/EP2004/002713, filed Mar. 16, 2004.

The present invention relates to the use of acylcyclohexanedione derivatives for improving the tolerance of plants to chilling temperatures and/or frost.

Temperature is one of the main factors which affect the growth and flourishing of plants. Chilling temperatures (of down to 0° C.) and frost (temperatures of below 0° C.) may slow down the germination and growth of plants and have a substantial effect on their development and on the quantity and quality of their products. Crop plants such as maize, sugarbeet, rice, soya, potato, tomato, bell pepper, melon, cucumber, bean, pea, banana and citrus species suffer injury and/or substantially delayed development even at temperatures of below 5° C. Even temperatures which are slightly below 0° C. lead to partial or complete death of these plant species. Late frosts around the time of flowering repeatedly lead to substantial yield losses for example in pome and stone fruit species such as apple, pear, quince, peach, nectarine, apricot, plum, quetsch, almond or cherry. Plants which have suffered chilling injury or frost damage show die-back symptoms, for example on leaves, flowers and buds. Frost-damaged flowers develop no fruit at all or else deformed fruit or fruit with skin damage, which can only be sold with difficulty, if at all. Severe chilling injury and frost damage entails the death of the entire plant.

Chilling injury and frost damage are therefore an important loss factor for the agricultural sector. Existing possibilities for avoiding chilling and frost damage are rather unsatisfactory owing to their complexity or the fact that the results are frequently not reproducible. Possibilities which must be mentioned in this context are the breeding of chill- and frost-resistant plant varieties, starting off chill-sensitive plants in the greenhouse and subsequently planting them out as late as possible, cultivation under plastic film, circulation of air in the stand, blowing in warm air, placing heaters in the stand, and irrigation frost protection.

DE 4437945 describes plant strengthening products comprising vitamin E, which are said to reduce the plant-injurious effect of phytotoxic agrochemicals and other abiotic stressors. These compositions may additionally comprise cryoprotectants such as glycerol. The cryoprotectant which is optionally present is not described as having an effect which prevents chill injury or frost damage.

J. Lalk and K. Dörffling described in Physiol. Plant. 63, 287-292 (1985) that abscisic acid can improve the frost resistance to chilling temperatures in hardened winter wheat.

EP-A 123 001 describes the use of acylcyclohexanedione compounds of the formula

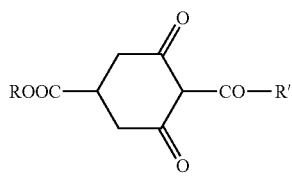

in which
R is hydrogen, alkyl, alkylthioalkyl or optionally substituted phenyl and R' is alkyl or optionally substituted benzyl, phenethyl, phenoxymethyl, 2-thienylmethyl, alkoxymethyl or alkylthiomethyl,
or salts of these as growth regulators. These compounds are also said to improve the chill resistance of rice seedlings, in addition to having a series of other advantageous effects. However, an improved chill resistance is demonstrated nowhere, nor does this publication provide information on the temperature range within which the chill-resistance-improving effect is meant to take place.

It is an object of the present invention to provide a composition by means of which the tolerance of plants to chilling temperatures and/or frost can be improved.

We have found that this object is achieved by the use of compounds of the formula I

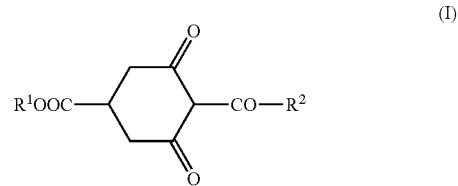

in which
$R^1$ is H or $C_1$-$C_{10}$-alkyl and
$R^2$ is $C_1$-$C_{10}$-alkyl or $C_3$-$C_{10}$-cycloalkyl or salts of these for improving the tolerance of plants to low temperatures.

In crop production, low temperatures are understood as meaning chilling temperatures and frost, i.e. temperatures of ≦15° C., preferably in the range of from 15° C. to −15° C., especially preferably of from 10° C. to −10° C. and in particular of from 10° C. to −5° C.

The compounds I which are used in accordance with the invention are preferably employed for improving the tolerance of plants to a temperature range of from −15 to 15° C., especially preferably of from −10 to 10° C. and in particular of from −5 to 10° C. In the case of chill-sensitive plants, compounds of the formula I are employed in particular for improving the tolerance of the plants to chilling temperatures. This is generally understood as meaning a tolerance to temperatures in the range of from 0 to 15° C., in particular of from 0 to 10° C. In the case of frost-sensitive plants—in addition to the abovementioned chill-sensitive plants, these are, for example, pome and stone fruit species during the flowering phase and citrus species and other plants which, while chill-resistant, are not frost-resistant—the compounds of the formula I are in particular also suitable for improving the tolerance of the plants to temperatures in the range of from −15° C. to 0° C., especially preferably of from −10° C. to 0° C., and in particular of from −5° C. to 0° C.

Tolerance is understood as meaning in particular the reduction or prevention of chilling injury and/or frost damage in plants.

The compounds of the formula I are especially preferably used for reducing or preventing chill injury in chill-sensitive crop plants such as maize, rice, soya, sugarbeet, aubergine, tomato, bell pepper, potato, melon, cucumber, bean, pea, banana and citrus species.

Moreover, the compounds of the formula I are especially preferably used in accordance with the invention for reducing or preventing frost damage in the abovementioned chill-sensitive crop plants, moreover in pome fruit and stone fruit and in all citrus species. In the case of the pome fruit and stone fruit species, these compounds are especially preferably used for preventing frost damage on the buds, flowers, leaves and young fruits of these plants. The pome fruit and stone fruit species are, for example, apple, pear, quince, peach, apricot, nectarine, cherry, plum, quetsch or almond, preferably apple. The citrus species are, for example, lemon, orange, grapefruit, clementine or tangerine.

In particular, the compounds of the formula I are used for reducing or preventing frost damage in pome fruit and stone fruit species, in particular in apple.

Acylcyclohexanedione compounds of the formula I are disclosed in EP-A 0 123 001 and in EP-A 126 713.

The compounds of the formula I can be present in the trione form (triketo form) I.a or else in the tautomeric keto-enol forms I.b and I.c, respectively:

Accordingly, the dianion contains both the carboxylate and the enolate groups.

Preferred cations in the salts of the compounds of the formula I are the ions of the alkali metals, preferably of lithium, sodium and potassium, of the alkaline earth metals, preferably of calcium and magnesium, and of the transition metals, preferably of manganese, copper, zinc and iron, moreover ammonium ($NH_4^+$) and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabu-

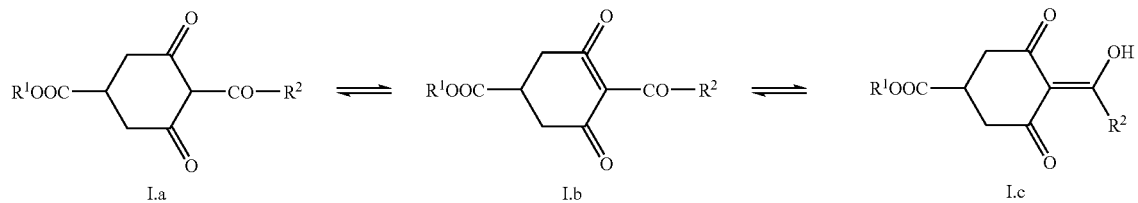

In the compounds of the formula I, $R^1$ is preferably H or $C_1$-$C_4$-alkyl.

$R^2$ is preferably $C_1$-$C_4$-alkyl or $C_3$-$C_6$-cycloalkyl and in particular ethyl or cyclopropyl.

In the definitions of the radicals $R^1$ and $R^2$, $C_1$-$C_{10}$-alkyl is a linear or branched alkyl radical, such as methyl, ethyl, propyl, isopropyl, n-butyl, sec-butyl, isobutyl, tert-butyl, pentyl, neopentyl, hexyl, heptyl, octyl, 2-ethylhexyl, nonyl or decyl. $C_1$-$C_4$-Alkyl is, for example, methyl, ethyl, propyl, isopropyl, n-butyl, sec-butyl, isobutyl or tert-butyl. The alkyl radical is preferably straight chain.

In the definition of $R^2$, $C_3$-$C_{10}$-cycloalkyl is, for example, cyclopropyl, cyclopentyl, cyclohexyl, cycloheptyl, cyclooctyl, cyclodecyl or decalin. $C_3$-$C_6$-Cycloalkyl is, for example, cyclopropyl, cyclopentyl or cyclohexyl.

The salts of the acylcyclohexanedione compounds I where $R^1 \neq H$ are the salts of monoanions, while, in the event that $R^1=H$, they may be both salts of the monoanions and the salts of the dianions of these compounds. The monoanions can be present not only as carboxylate anions I.d, but also as enolate anions I.e and I.f, respectively:

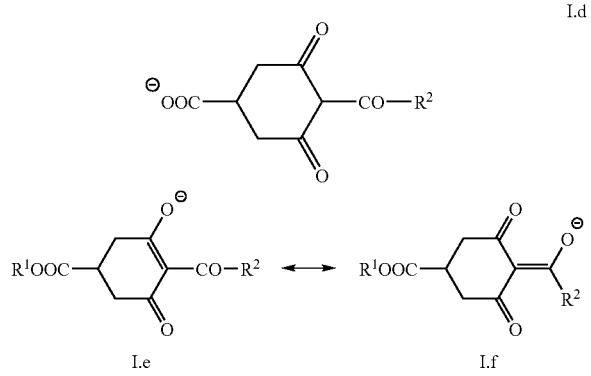

tylammonium, 2-hydroxyethylammonium, 2-(2-hydroxyeth-1-oxy)eth-1-ylammonium, di(2-hydroxyeth-1-yl)ammonium, benzyltrimethylammonium, benzyltriethylammonium, moreover phosphonium ions, sulfonium ions, preferably tri($C_1$-$C_4$-alkyl)sulfonium such as trimethylsulfonium and sulfoxonium ions, preferably tri($C_1$-$C_4$-alkyl)sulfoxonium. Preferred cations are furthermore chlormequat [(2-chloroethyl)trimethylammonium], mepiquat (N,N-dimethylpiperidinium) and N,N-dimethylmorpholinium. Particularly preferred cations are the alkali metal cations, the alkaline earth metal cations and the ammonium cation ($NH_4^+$). It is, in particular, the calcium salt.

Compounds which are used especially preferably in accordance with the invention are prohexadione ($R^1$=H, $R^2$=ethyl), prohexadione-calcium (prohexadione calcium salt), trinexapac ($R^1$=H, $R^2$=cyclopropyl) and trinexapac-ethyl ($R^1$=ethyl, $R^2$=cyclopropyl). Prohexadione, in particular prohexadione-calcium, is used specifically.

For the purposes of the present invention, the term "compounds of the formula I" refers both to the neutral compounds I and to their salts.

The compounds of the formula I are preferably employed at an application rate of 25 to 1000 g/ha, especially preferably 50 to 500 g/ha and in particular 50 to 250 g/ha.

In a preferred embodiment, the compounds of the formula I are used in accordance with the invention in combination with vitamin E or a derivative thereof and/or with abscisic acid and/or with a customary cryoprotectant as adjuvant.

The weight ratio of compounds of the formula I to vitamin E or its derivatives is preferably 1:1 to 1:20, especially preferably 1:5 to 1:20 and in particular 1:5 to 1:15. The weight ratio of compounds of the formula I to abscisic acid is preferably 1:0.05 to 1:1, especially preferably 1:0.05 to 1:0.5 and in particular 1:0.1 to 1:0.3. The weight ratio of compounds of the formula I to the cryoprotectant is preferably 1:10 to 1:1 000, especially preferably 1:10 to 1:500 and in particular 1:10 to 1:100.

For the purposes of the present invention, vitamin E is understood as meaning all compounds of the vitamin E group, for example the α- to η-tocopherols and the tocotrienols and their isomers, salts and esters, it being irrelevant whether these compounds are of natural or synthetic origin. Substances which are particularly preferably used are α-tocopherol, which occurs naturally (RRR-α-tocopherol) or an ester thereof with a $C_1$-$C_4$-carboxylic acid, such as formic acid, acetic acid, propionic acid or butyric acid. α-Tocopherol acetate is used in particular.

Abscisic acid is (S)(+)-5-(1-hydroxy-2,6,6-trimethyl-4-oxo-2-cyclohexenyl)-3-methyl-cis/trans-2,4-pentadienoic acid, of the formula

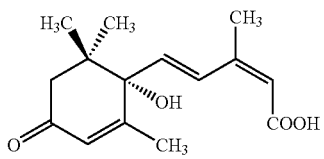

Cryoprotectants which are suitable for the treatment of plants encompass alcohols such as propanol and butanol, polyols such as glycol or glycerol, (poly)ether polyols such as diethylene glycol, triethylene glycol and polyethylene glycols with a molecular weight of up to 500. A cryoprotectant which is preferably used is glycerol.

The compounds of the formula I, or their combination with the abovementioned adjuvants, are typically employed as formulations as they are conventionally used in the field of crop protection.

For example, their concentrated solutions, suspensions or emulsions can be diluted with water and applied by spraying. The use forms depend on the type of plant or the plant part to which it is to be applied; in any case, they should allow as fine as possible a distribution of the active substances and adjuvants.

In addition to the compounds of the formula I, if appropriate as a combination with vitamin E and/or abscisic acid and/or the cryoprotectant, the formulations may comprise formulation auxiliaries as are conventionally used for the formulation of crop protection products, for example inert adjuvants and/or surface-active substances such as emulsifiers, dispersants, wetters and the like.

Suitable surface-active substances are the alkali metal, alkaline earth metal and ammonium salts of aromatic sulfonic acids, for example lignosulfonic acid, phenolsulfonic acid, naphthalene-sulfonic acid and dibutylnaphthalenesulfonic acid and of fatty acids, alkyl- and alkylarylsulfonates, alkyl, lauryl ether and fatty alcohol sulfates, and the salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, lignin sulfite waste liquors, methylcellulose or siloxanes. Examples of suitable siloxanes are polyether/polymethylsiloxane copolymers, which are also referred to as spreaders or penetrants.

Inert formulation auxiliaries are essentially:

mineral oil fractions of medium to high boiling point such as kerosene and diesel oil, furthermore coal tar oils and oils of vegetable or animal origin, aliphatic, cyclic and aromatic hydrocarbons, for example paraffins, tetrahydronaphthalene, alkylated naphthalenes and their derivatives, alkylated benzene and their derivatives, alcohols such as methanol, ethanol, propanol, butanol and cyclohexanol, ketones such as cyclohexanone, strongly polar solvents, for example amines such as N-methylpyrrolidone, and water.

Aqueous use forms of the compounds I or their combination with vitamin E and/or abscisic acid and/or the cryoprotectant can be prepared from storage formulations such as emulsion concentrates, suspensions, pastes, wettable powders or water-dispersible granules by addition of water. To prepare emulsions, pastes or oil dispersions, the compounds of the formula I or their abovementioned combination with vitamin E and/or abscisic acid and/or the cryoprotectant, as such or dissolved in an oil or solvent, can be homogenized in water by means of wetter, sticker, dispersant or emulsifier. Naturally, the use forms will comprise the adjuvants used in the storage formulations.

In a preferred embodiment, the compounds of the formula I or their abovementioned combination are used in the form of an aqueous spray mixture. The aqueous spray mixture comprises the compounds of the formula I in an amount of preferably from 50 to 200 ppm. When the abovementioned combination is used as spray mixture, it will comprise vitamin E in an amount of preferably from 50 to 4 000 ppm, especially preferably from 500 to 3 500 ppm and in particular from 1 000 to 3 000 ppm; abscisic acid in an amount of preferably from 0 to 200 ppm, especially preferably of from 2.5 to 100 ppm and in particular of from 5 to 15 ppm, and the cryoprotectant in an amount of preferably from 0 to 50 000 ppm, especially preferably from 500 to 20 000 ppm, and in particular from 500 to 10 000 ppm.

The components acylcyclohexanedione I, vitamin E and/or abscisic acid and/or the cryoprotectant can be applied to the plant or the plant parts as a mixture or separately; in the latter case, the individual components should be applied within as short an interval as possible.

The acylcyclohexanediones I which are used in accordance with the invention can be employed for application in all of the abovementioned plants, but also in plant species which differ from them. Depending on the plant part to which they are to be applied, they can be applied with apparatuses which are known per se and conventionally used in agricultural practice, application in the form of an aqueous spray solution or spray mixture being preferred.

Application is preferably effected by spraying to run-off point. Either all of the aerial plant part or else only individual plant parts, such as flowers, leaves or fruits, are treated. The choice of the individual plant parts to be treated depends on the species of the plant and its developmental stage. It is preferred to treat the sprouts, seedlings, buds and flowers in various developmental stages, and the young fruits.

Application is preferably effected prior to a period of chilling temperature or frost. It is preferably effected at least 12 hours, especially preferably at least 24 hours and in particular 36 hours to 20 days before the expected onset of chilling temperatures or frost.

The present invention furthermore relates to a method for improving the tolerance of plants to low temperatures, preferably for reducing or preventing chilling injury and frost damage in plants, which comprises applying an aqueous composition comprising compounds of the formula I to plants or plant parts.

What has been said above with regard to the compounds of the formula I, other components, the aqueous composition and the application applies here analogously.

The tolerance of plants to chilling temperatures and frost is increased markedly by the use according to the invention of the acylcyclohexanediones I. In particular, chilling injury and frost damage on plants are prevented or at least reduced by the use according to the invention. A further advantage of the use according to the invention of acylcyclohexanediones I, specifically of prohexadione-calcium, is their activity against fireblight. Accordingly, the plants treated in accordance with the invention are not only more resistant to lower temperatures, but are additionally protected against this floral infection.

The examples which follow are intended to illustrate the invention, but without imposing any limitation.

EXAMPLES

1. Reduction/Prevention of Frost Damage on Apple Flowers

To study the effect of compounds I used in accordance with the invention, flower buds or flowers of various apple varieties were sprayed to run-off point at different stages and different points in time with prohexadione-calcium in the form of the commercial preparation Regalis® from BASF AG in the form of 10% strength granules with 250 ppm of active substance or with a mixture of vitamin E and glycerol (see treatments a) to d)) and subjected to a naturally occurring or simulated frost event during mid-bloom. The treated flowering branches and untreated flowering branches which had been subjected to the same frost event and which acted as control, were subsequently transferred for 2 to 4 days into a greenhouse with temperatures ranging from 15 to 25° C., and the floral injury was assessed.

1.1 Simulated Frost Event 1.1.1

Apple branches with flower buds or flowers (R. Cox) were treated as specified under a.1), b.1), c.1) or d.1) and subsequently subjected to a simulated frost event.

Treatment:

a.1) Apple buds sprayed to run-off point with prohexadione-calcium nine days prior to the simulated frost event.

b.1) Apple flowers (mid-bloom) sprayed to run-off point with prohexadione-calcium one day prior to the simulated frost event.

c.1) Apple flowers (mid-bloom) sprayed to run-off point with a mixture of vitamin E (2 500 ppm) and glycerol (50 000 ppm) one day prior to the simulated frost event.

d.1) Apple flowers (mid-bloom) sprayed to run-off point with a mixture of vitamin E (2 500 ppm), glycerol (50 000 ppm) and Break Thru (1 000 ppm; siloxane spreader from Goldschmidt AG, Essen) one day prior to the simulated frost event.

Nine days (a.1)) or one day (b.1)-d.1)) after the treatment, the treated flowering branches and untreated control branches were cut off and subjected to a simulated frost event. The temperature program of the simulated frost event was as follows:

chilling from 12° C. to 4° C. within 30 minutes
one hour at 4° C.
chilling from 4° C. to 2° C. within 15 minutes
75 minutes at 2° C.
chilling from 2° C. to −3° C. within 30 minutes
150 minutes at −3° C.

Two days after the frost event, the floral damage was assessed by examining the individual flowers. At the time of evaluation, the flowers were in the floral stage BBCH 54-56 (BBCH=Biologische Bundesanstalt für Land- und Forstwirtschaft, Bundessortenamt und Chemische Industrie [Federal Biological Institute for Agriculture and Forestry, Federal Office for Crop Plant Varieties, Chemical Industry]). Those flowers whose ovary is brownish in color are considered as damaged (destroyed). The results are listed in Table 1 hereinbelow. The data which represent the percentage of damaged flowers correspond to the mean±standard deviation. A statistically significant difference (critical difference: 5%) between the means of the various measurement series is identified by different letters.

TABLE 1

| Treatment | Percentage of damage to flowers [%] | Significance |
|---|---|---|
| Control (untreated) | 29.6 ± 2.6 | a |
| a.1) | 15.6 ± 2.5 | b |
| b.1) | 23.1 ± 2.4 | ab |
| c.1) | 25.1 ± 3.3 | a |
| d.1) | 21.9 ± 2.5 | ab |

As shown in Table 1, floral damage is shown by significantly fewer apple flowers which have been treated with prohexadione-calcium nine days prior to the frost event than by untreated flowers.

1.1.2

Apple branches with flower buds or flowers (R. Cox) were treated analogously to Example 1.1.1, but remained for 210 minutes in the frost chamber at −3° C. The results are shown in Table 2.

TABLE 2

| Treatment | Percentage of damage to flowers [%] | Significance |
|---|---|---|
| Control (untreated) | 34.6 ± 2.6 | a |
| a.1) | 6.0 ± 1.2 | d |
| b.1) | 33.3 ± 2.6 | a |
| c.1) | 24.3 ± 2.1 | b |
| d.1) | 15.6 ± 2.1 | c |

As shown in Table 2, floral damage is shown by significantly fewer apple flowers which have been treated with prohexadione-calcium nine days prior to the frost event than by untreated flowers or by flowers which have been treated only two days prior to the frost event.

1.1.3

Apple branches with flower buds or flowers (Jonagold) were treated analogously to Example 1.1.1. They remained for 150 minutes in the frost chamber at −3° C. At the time of evaluation, the flowers were in floral stage BBCH 56-57. The results are shown in Table 3.

TABLE 3

| Treatment | Percentage of damage to flowers [%] | Significance |
|---|---|---|
| Control (untreated) | 71.9 ± 2.7 | a |
| a.1) | 54.4 ± 3.2 | b |
| b.1) | 69.0 ± 2.9 | a |
| c.1) | 74.7 ± 2.7 | a |
| d.1) | 56.1 ± 3.0 | b |

As shown in Table 3, floral damage is shown by significantly fewer apple flowers which have been treated with prohexadione-calcium nine days prior to the frost event than by untreated flowers or by flowers which have been treated only two days prior to the frost event.

1.1.4

Apple branches with flower buds or flowers (Jonagold) were treated analogously to Example 1.1.3, but remained for 210 minutes in the frost chamber at −3° C. The results are shown in Table 4.

TABLE 4

| Treatment | Percentage of damage to flowers [%] | Significance |
|---|---|---|
| Control (untreated) | 77.4 ± 2.2 | a |
| a.1) | 43.8 ± 4.2 | c |
| b.1) | 66.0 ± 2.7 | b |
| c.1) | 49.3 ± 2.7 | c |
| d.1) | 67.2 ± 2.7 | b |

As shown in Table 4, significantly less damage is shown in particular by flowers which have been treated with prohexadione-calcium nine days prior to the frost event, but also by those which were treated 2 days prior to the frost event.

1.1.5

Apple branches with flower buds or flowers (Gala) were treated as described under a.2), b.2), c.2) or d.2) and subsequently subjected to a simulated frost event.

Treatment:

a.2) Apple buds were sprayed to run-off point with prohexadione-calcium eleven days prior to the simulated frost event.

b.2) Apple flowers (mid-bloom) were sprayed to run-off point with prohexadione-calcium two days prior to the simulated frost event.

c.2) Apple flowers (mid-bloom) were sprayed to run-off point with a mixture of vitamin E (2 500 ppm) and glycerol (50 000 ppm) two days prior to the simulated frost event.

d.2) Apple flowers (mid-bloom) were sprayed to run-off point with a mixture of vitamin E (2 500 ppm), glycerol (50 000 ppm) and Break Thru (1 000 ppm; siloxane spreader from Goldschmidt AG, Essen) two days prior to the simulated frost event.

11 days (a.2)) or two days (b.2)-d.2)) after the treatment, the treated flowering branches and untreated control branches were cut off and subjected to a simulated frost event. The temperature program of the simulated frost event corresponded to the one in Example 1.1.1. Four days after the frost event, the floral damage was assessed by examining the individual flowers. At the time of evaluation, the flowers were in floral stage BBCH 57-59. The results are shown in Table 5.

TABLE 5

| Treatment | Percentage of damage to flowers [%] | Significance |
|---|---|---|
| Control (untreated) | 8.0 ± 1.9 | b |
| a.2) | 5.2 ± 1.8 | b |
| b.2) | 8.8 ± 2.5 | b |
| c.2) | 3.8 ± 1.7 | b |
| d.2) | 23.9 ± 3.2 | a |

As shown in Table 5, treatment with prohexadione-calcium 11 days prior to the frost event tends to reduce the damage.

1.1.6

Apple branches with flower buds or flowers (Boskoop) were treated analogously to Example 1.1.5. At the time of evaluation, the flowers were in floral stage BBCH 59-61. They remained at −3° C. for 150 minutes. The results are shown in Table 6.

TABLE 6

| Treatment | Percentage of damage to flowers [%] | Significance |
|---|---|---|
| Control (untreated) | 69.4 ± 4.4 | b |
| a.2) | 33.6 ± 4.1 | c |
| b.2) | 36.8 ± 4.2 | c |
| c.2) | 61.8 ± 4.2 | b |
| d.2) | 82.5 ± 3.9 | a |

As shown in Table 6, floral damage was shown by significantly fewer flowers which had been treated with prohexadione-calcium prior to the frost event than by those which had been treated with vitamin E/glycerol or not at all.

1.2 Naturally Occurring Frost Event 1.2.1

Apple branches with flower buds or flowers (R. Cox) were treated as described under a.3), b.3), c.3) or d.3) and subsequently subjected to a naturally occurring frost event.

Treatment:

a.3) Apple buds were sprayed to run-off point with prohexadione-calcium ten days prior to the frost event.

b.3) Apple flowers (mid-bloom) were sprayed to run-off point with prohexadione-calcium two days prior to the frost event.

c.3) Apple flowers (mid-bloom) were sprayed to run-off point with a mixture of vitamin E (2 500 ppm) and glycerol (50 000 ppm) two days prior to the frost event.

d.3) Apple flowers (mid-bloom) were sprayed to run-off point with a mixture of vitamin E (2 500 ppm), glycerol (50 000 ppm) and Break Thru (1 000 ppm; siloxane spreader from Goldschmidt AG, Essen) two days prior to the frost event.

The frost period lasted 5 days. The lowest temperature was reached on day two of the frost event and was −4° C. One day after the frost event, the treated flowering branches and untreated control branches were cut off. One day after the branches had been cut off, the floral damage was assessed by examining the individual flowers. At the time of evaluation, the flowers were in floral stage BBCH 56-57. The results are shown in Table 7.

TABLE 7

| Treatment | Percentage of damage to flowers [%] | Significance |
|---|---|---|
| Control (untreated) | 100 ± 0 | a |
| a.3) | 88.3 ± 1.3 | b |
| b.3) | 76.6 ± 1.7 | c |
| c.3) | 89.2 ± 1.2 | b |
| d.3) | 90.8 ± 1.3 | b |

As shown in Table 7, all treatments, but in particular those with prohexadione-calcium, resulted in reduced floral damage.

1.2.2

Apple branches with flower buds or flowers (Jonagold) were treated analogously to Example 1.2.1 and exposed to the same frost event. At the time of evaluation, the flowers were in floral stage BBCH 57-59. The results are shown in Table 8.

TABLE 8

| Treatment | Percentage of damage to flowers [%] | Significance |
|---|---|---|
| Control (untreated) | 74.5 ± 2.2 | a |
| a.3) | 67.5 ± 2.3 | b |

TABLE 8-continued

| Treatment | Percentage of damage to flowers [%] | Significance |
|---|---|---|
| b.3) | 67.7 ± 2.6 | b |
| c.3) | 65.1 ± 2.1 | b |
| d.3) | 64.2 ± 2.5 | b |

As shown in Table 8, all the treatments resulted in reduced floral damage.

1.2.3

Apple branches with flower buds or flowers (Boskoop) were treated as described under a.4), b.4), c.4) or d.4) and subsequently subjected to a naturally occurring frost event.

Treatment:

a.4) Apple buds were sprayed to run-off point with prohexadione-calcium thirteen days prior to the frost event.

b.4) Apple flowers (mid-bloom) were sprayed to run-off point with prohexadione-calcium five days prior to the frost event.

c.4) Apple flowers (mid-bloom) were sprayed to run-off point with a mixture of vitamin E (2 500 ppm) and glycerol (50 000 ppm) five days prior to the frost event.

d.4) Apple flowers (mid-bloom) were sprayed to run-off point with a mixture of vitamin E (2 500 ppm), glycerol (50 000 ppm) and Break Thru (1 000 ppm; siloxane spreader from Goldschmidt AG, Essen) five days prior to the frost event.

The frost period lasted for one day. The lowest temperature was −1.2° C. Two days after the frost event, the treated flowering branches and untreated control branches were cut off, and one day after the branches had been cut off, the floral damage was assessed by examining the individual flowers. At the time of evaluation, the flowers were in floral stage BBCH 57-61. The results are shown in Table 9.

TABLE 9

| Treatment | Percentage of damage to flowers [%] | Significance |
|---|---|---|
| Control (untreated) | 94.0 ± 2.4 | ab |
| a.4) | 84.3 ± 3.3 | bc |
| b.4) | 74.7 ± 3.0 | d |
| c.4) | 95.6 ± 2.5 | a |
| d.4) | 75.5 ± 4.1 | c |

As shown in Table 9, floral damage is shown by significantly fewer flowers which have been treated with prohexadione-calcium 5 days prior to the frost event than by those which had been treated with prohexadione-calcium 13 days prior to the frost event, or with vitamin E/glycerol 5 days prior to the frost event or not at all.

2. Stabilization of the Photochemical Efficacy of the Electron Transport in Apple Seedlings Intact photosynthesis in leaves and other green plant tissues is of utmost importance for frost resistance and the intensity of the subsequent regeneration processes. To study the effect of compounds I which were used in accordance with the invention, the photosynthesis rate of treated (a.5) to (e.5)) and untreated apple seedlings which had been subjected to a simulated frost event was determined.

The material used for the experiments was apple seedlings which had been grown from seeds of Golden Delicious apples following cold stratification under controlled-environment cabinet conditions (temperature approx. 20° C.; relative atmospheric humidity approx. 70° C.; day:night=10.5:13.5 hours; light intensity approx. 200 µmol m$^{-2}$ s$^{-1}$) and which had three to four fully formed leaves at the point in time of treatment. Batches of 10 plants per combination were treated as follows:

a.5) Spraying to run-off point with 50 ppm prohexadione-calcium 21 days prior to the simulated frost event.

b.5) Spraying to run-off point with 50 ppm prohexadione-calcium 8 days prior to the simulated frost event.

c.5) Spraying to run-off point with 50 ppm prohexadione-calcium 2 days prior to the simulated frost event.

d.5) Spraying to run-off point with a mixture of vitamin E (2 500 ppm) and glycerol (50 000 ppm) 2 days prior to the simulated frost event.

e.5) Spraying to run-off point with a mixture of vitamin E (2 500 ppm), glycerol (50 000 ppm) and Break Thru (1 000 ppm; siloxane spreader from Goldschmidt AG, Essen) 2 days prior to the simulated frost event.

To simulate the frost event, the plants were subjected to the following chill program:

removal from the controlled-environment cabinet (20° C.)

transfer into the chill cell to randomized positions at a height of approximately 40 cm for approx. 6 hours at 12° C.

2 hours at 4° C.

1.5 hours at 2° C.

1 hour at 0° C.

3.5 hours at −3° C.

controlled-environment cabinet (20° C.)

The photosynthesis rate of the stressed apple seedlings was subsequently determined with the aid of a pulse amplitude modulation fluorometer (PAM 2000, Heinz Walz GmbH, Effeltrich). The quotient $F_v/F_m$, which is determined, describes the amount of light energy captured by the photosynthesis apparatus of the plants which can be exploited for the production of assimilates. $F_v$ represents the variable fluorescence, which corresponds to the difference between $F_0$ (basal fluorescence, which is measured when a dark-adapted leaf is irradiated with fluorescence-exciting light) and $F_m$ (maximum fluorescence of a dark-adapted leaf) ($F_v/F_m=(F_m-F_0)/F_m$). Table 10 shows the results obtained 24 hours after the frost event.

TABLE 10

| Treatment | $F_v/F_m$ |
|---|---|
| Control without frost | 0.801 |
| Control with frost | 0.755 |
| a.5) | 0.812 |
| b.5) | 0.809 |
| c.5) | 0.804 |
| d.5) | 0.765 |
| e.5) | 0.804 |

As shown in Table 10, in particular the prohexadione-calcium-treated apple seedlings survived the frost event virtually undamaged, while the untreated plants which had been exposed to the simulated frost event show a markedly reduced photosynthesis rate.

These results also demonstrate that not only flowers, but also vegetative tissue of crop plants, are protected from the effects of lower temperatures by prohexadione-calcium.

We claim:

1. A method for reducing or preventing in pome or stone fruit plants or in citrus plants frost damage caused by temperatures in the range of from −15° to 0° C., comprising applying to said plants or plant parts 36 hours to 20 days before a cold or frost spell a plant-protecting effective amount of at least one compound of formula I

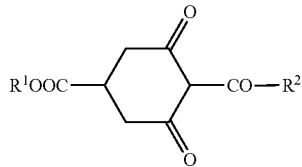

wherein
$R^1$ is H or $C_1$-$C_{10}$-alkyl, and $R^2$ is $C_1$-$C_{10}$-alkyl or $C_3$-$C_{10}$-cycloalkyl, or a biologically acceptable salt thereof.

2. The method according to claim 1, wherein said compound of formula (I) is in the form of an aqueous composition.

3. The method according to claim 1, wherein the method reduces or prevents chilling injury on flowers, young fruits and seedlings.

4. The method according to claim 1, wherein alkali metal, alkaline earth metal, transition metal, ammonia, substituted ammonium, sulfonium, phosphonium or sulfoxonium salts of compounds of the formula I where $R^1$=H are employed.

5. The method according to claim 4, wherein the calcium salt is used.

6. The method according to claim 5, where $R^2$ is ethyl.

7. The method according to claim 1 where $R^1$ is ethyl and $R^2$ is cyclopropyl.

8. The method according to claim 1, wherein said compound of formula (I) is applied in combination with one or more of vitamin E, abscisic acid, or conventional cryoprotectants.

9. The method according to claim 8, wherein the cryoprotectant is glycerol.

10. The method according to claim 8, wherein the compound of the formula I and vitamin E are employed in a weight ratio of from 1:1 to 1:20, respectively.

11. The method according to claim 8, wherein the compound of the formula I and abscisic acid are employed in a weight ratio of from 1:0.05 to 1:1, respectively.

12. The method according to claim 1, wherein the compound of the formula I and/or a salt thereof is employed in the form of an aqueous spray composition comprising the compound of the formula I and/or salt thereof in an amount of from 5 to 1000 ppm.

13. The method according to claim 1, wherein the application rate of the compound of the formula I is in the range of from 25 to 1000 g/ha.

14. A method for reducing or preventing in pome or stone fruit plants or in citrus plants frost damage caused by temperatures in the range of from −15° to 0° C., comprising applying to aerial plant parts of said plants 36 hours to 20 days before a cold or frost spell a plant-protecting effective amount of at least one compound of formula I

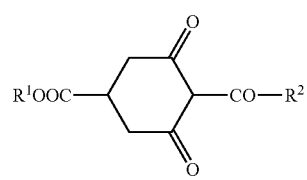

wherein
$R^1$ is H or $C_1$-$C_{10}$-alkyl, and
$R^2$ is $C_1$-$C_{10}$-alkyl or $C_3$-$C_{10}$-cycloalkyl,
or a biologically acceptable salt thereof.

* * * * *